United States Patent [19]

Ricciardelli

[11] 4,273,134
[45] Jun. 16, 1981

[54] FIXATION RING ASSEMBLY AND METHOD OF ASSEMBLING A SENSOR HEAD

[75] Inventor: Robert H. Ricciardelli, Waukesha, Wis.

[73] Assignee: Biochem International Inc., Wauwatosa, Wis.

[21] Appl. No.: 41,524

[22] Filed: May 22, 1979

[51] Int. Cl.$^3$ ............................................. A61B 5/00
[52] U.S. Cl. ................................... 128/635; 29/453; 29/570; 204/195 B; 204/195 P
[58] Field of Search .............................. 128/635, 632; 204/195 B, 195 P; 29/570, 453

[56] References Cited

U.S. PATENT DOCUMENTS

| 3,795,239 | 3/1974 | Eberhard et al. | 128/635 |
| 3,875,037 | 4/1975 | Krull | 204/195 P |
| 3,959,061 | 5/1976 | Renck et al. | 29/453 X |

FOREIGN PATENT DOCUMENTS

2724461 12/1977 Fed. Rep. of Germany ........... 128/635

OTHER PUBLICATIONS

Vesterager, "Transcutaneous $Po_2$ Electrode", Scand. J. Clin. Lab. Invest., 37 (Supp 146), pp. 27–30, 1977.
Eberhard et al., "Continuous $Po_2$... Electrodes", Med. & Biol. Eng., vol. 13, No. 3, pp. 436–442, May 1975.

*Primary Examiner*—Lee S. Cohen
*Attorney, Agent, or Firm*—Richard G. Lione

[57] ABSTRACT

A method of assembling a sensor head and permeable membrane with encapsulated electrolyte. A disposable fixation ring is part of a similarly disposable fixation ring assembly, the latter of which serves as a fixture for automatically mounting the membrane on the sensor head body with the electrolyte encapsulated. The ring is then employed to fasten the head to a patient's skin while the remainder of the assembly is discarded, the ring also being disposable after use on a patient.

10 Claims, 7 Drawing Figures

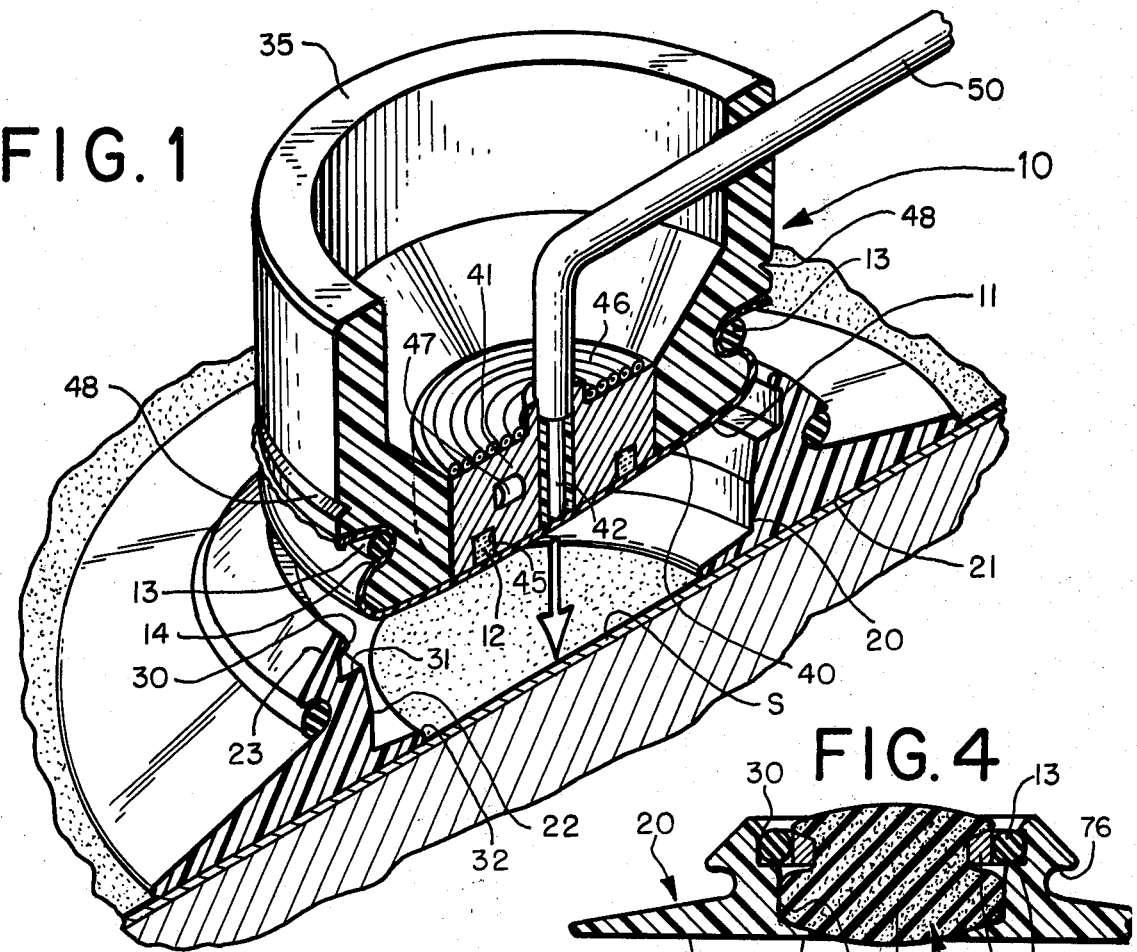

FIXATION RING ASSEMBLY AND METHOD OF ASSEMBLING A SENSOR HEAD

FIELD OF THE INVENTION

This invention is generally in the field of medical technology as it relates to monitoring a patient's oxygen level. It relates particularly to the continuous monitoring of a patient's oxygen level by non-intrusive means.

BACKGROUND OF THE INVENTION

Non-intrusive monitoring of a patient's oxygen level is well known in medical technology. It is conventional, for example, to fasten a sensor head incorporating a polarographic oxygen sensor to the skin of a patient through the medium of a fixation ring.

The fixation ring is normally attached to the patient's skin in a suitable location with an adhesive. The sensor head is releasably held in the ring and comprises an insulating matrix having an anode and a cathode embedded therein. The anode and cathode are electrically insulated from each other but exposed at an electrochemically active base surface.

An anion exchange resin electrolyte is encapsulated between an oxygen diffusion material in the form of a permeable membrane and the base surface. The membrane presses against the patient's skin and oxygen from the patient's system flows through it to be monitored by a system of which the sensor head-membrane-electrolyte assembly is a part.

After each use of a fixation ring and sensor head-membrane-electrolyte assembly for monitoring purposes the permeable membrane is removed and discarded. It is also conventional to discard the fixation ring since it is a very inexpensive component. The sensor head, on the other hand, is reused.

Before every use of a sensor head it must be refitted with a permeable membrane encapsulating a suitable amount of electrolyte. To this end it is conventional to provide the medical facility with mounting tools for mating a permeable membrane to the sensor head. The mounting tools require some expertise to use. The process is relatively laborious and time consuming.

SUMMARY OF THE INVENTION

It is an object of the present invention to provide a new and improved method of assembling a sensor head and permeable membrane with encapsulated electrolyte.

It is another object to provide a new and improved method of assembling a sensor head and permeable membrane with encapsulated electrolyte wherein the assembly can be accomplished quickly and simply without tools.

It is still another object to provide a disposable fixation ring assembly which also serves as a fixture for automatically mounting the membrane on the sensor body with the electrolyte encapsulated.

The foregoing and other objects are realized in accord with the present invention by providing a disposable fixation ring assembly including a ring member. The ring member has a lower face for fastening with adhesive to the surface of a patient's skin, an upper face, and an annular passage through the ring between the faces. A semi-permeable membrane is stretched over the upper face and retained on an annular shoulder encircling the passage by a resilient outer O-ring.

Mounted in the passage is a compression pad formed of low density foam material. A rigid ring fabricated of brass encircles and partially compresses the pad. A resilient inner O-ring encircles the rigid ring and is held in extended relationship by the rigid ring.

The permeable membrane holds the compression pad in place in the passage through the ring member. The permeable membrane is annularly serrated adjacent its retaining outer O-ring.

To mount the permeable membrane on a sensor head with electrolyte encapsulated therebetween, the aforedescribed fixation ring assembly is placed on a flat surface with its lower face down. One drop of a suitable electrolyte is then placed on the base surface of the sensor body in the electrochemically active region. The sensor body is positioned directly over the passage through the fixation ring and pressed downwardly into it.

Upon encountering the membrane the base surface of the sensor body has the membrane forced up against it by the sponge compression pad below the membrane. This serves to force excess electrolyte outwardly from the electrochemically active region, leaving a precise and predetermined amount of electrolyte in the region.

Further movement of the sensor head downwardly through the passage in the fixation ring member also forces the sponge rubber pad and its encircling rigid ring downwardly. The inner O-ring encircling the rigid ring is prevented from moving downwardly by a shoulder within the fixation ring member passage. As a result this inner O-ring contracts radially inwardly against the annular lower periphery of the sensor head.

In the meantime, as the membrane is forced downwardly with the sponge by the sensor head it tears away from the outer O-ring at the serration. When the inner O-ring is released from the rigid retaining ring and snaps against the side of the sensor head it captures the periphery of the membrane against the sensor head with the electrolyte encapsulated between the membrane and the electrolytically active region of its base surface.

The sensor head is then pulled out of the fixation ring member. It has the membrane securely mounted in place. The rigid ring is left loosely seated within the passage in the fixation ring member and can be easily removed and discarded. Such is also the case with the sponge rubber pad.

The fixation ring is then used for its primary function, attachment via an adhesive on its base to the skin of the patient in the area where sensing is to take place. After that is done the sensing head is again pressed into the passage in the fixation ring member. This time, however, it is pressed in until it is held by a retaining shoulder. The system is then ready for monitoring.

BRIEF DESCRIPTION OF THE DRAWINGS

The invention, including its construction and method of operation, together with additional objects and advantages thereof, is illustrated more or less diagrammatically in the drawings, in which:

FIG. 1 is a sectional view, in perspective, of a fixation ring attached to the skin surface of a patient and a sensor head-membrane-electrolyte assembly about to be seated in the fixation ring;

FIG. 2 is a sectional view through the inner O-ring and rigid ring sub-assembly;

FIG. 3 is a sectional view through a compression pad, inner O-ring, and rigid ring sub-assembly;

FIG. 4 is a sectional view through a partially completed fixation ring assembly;

FIG. 5 is a sectional view through a disposable fixation ring assembly;

DESCRIPTION OF THE PREFERRED EMBODIMENT

Figure 6:
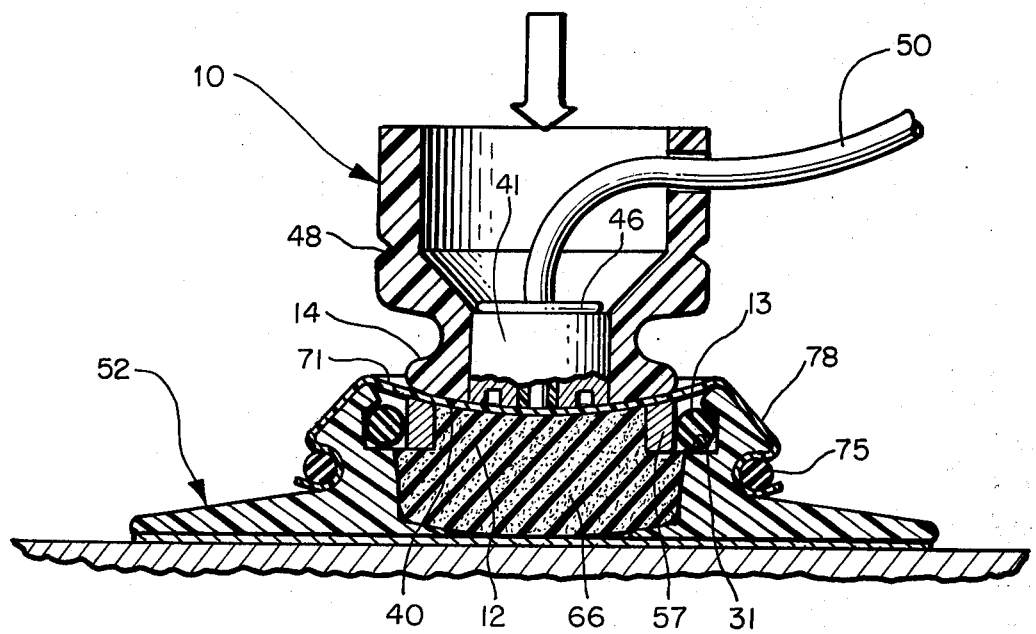
FIG. 6 is a sectional view through a disposable fixation ring assembly with a sensor head being inserted to automatically fasten the membrane to the sensor head and encapsulate electrolyte therebetween.

Referring now to the drawings, and particularly FIG. 1, a sensor head 10 and a permeable membrane 11 are shown assembled with an electrolyte 12 encapsulated between them. The permeable membrane 11 is retained in assembled relationship with the sensor head 10 by an inner O-ring 13 encircling the head and seated in an annular recess 14.

The sensor head 10-membrane 11-electrolyte 12 assembly is shown just as it is about to be seated in a fixation ring member 20 fastened to the skin S of a patient. The ring member 20 has a flat lower face 21 which is fastened to the patient's skin with a suitable adhesive. The sensor head-permeable membrane-electrolyte assembly is inserted into the fixation ring member 20 and gripped thereby for operation of the oxygen sensing system in a conventional manner.

Referring to FIGS. 1 and 4, the fixation ring member 20 is molded of Delrin or the like and has an axial passage 22 extending through it from its lower face to an upper face 23. An annular lip 30 is formed around the passage 22 adjacent the upper face 23. This lip 30 is designed to releasably grip the sensor head 10.

An inwardly extending upper shoulder 31 is formed in the passage 22 below the lip 30. The passage 22 has a smaller diameter section below the shoulder 31. The passage 22 terminates at the bottom surface 21 through an inwardly extending lower shoulder 32.

Referring to FIG. 1, the sensor head 10 comprises a Delrin body 35 having an annular configuration designed to fit within the passage 22 in the fixation ring member 20. The body 35 has a curved lower face 40; i.e., it has a spherical configuration with the diameter of the sphere being sufficiently large to make the curvature slight.

The sensor head 10 includes a silver disc 41 at the lower face 40 which forms an anode. A central cathode 42 formed of platinum extends upwardly through the anode and is insulated from it. Both anode and cathode are exposed at the lower face 40, however. A channel 45 formed upwardly into the lower face 40 (and the anode 41) encircles the cathode 42 and serves as an electrolyte film reservoir. The anode 41 also contains a conventional heater coil 46 and thermistor 47 as will be seen.

A patient cable 50 extends from the Delrin body 35 to a quick disconnect connector (not shown) which is used to connect it to an amplifier in the monitoring device. The patient cable 50 includes heater leads and anode-/cathode leads. It also includes conventional heater and thermistor leads.

The inner O-ring 13 encircles the head 10 immediately above the head's curved lower face 40. Immediately above the O-ring 13, on a larger diameter of the head 10, is an annular locking notch 48. The lip 30 on the ring member 20 snaps into the notch 48 to hold the head 10 in the fixation ring when it is fully seated.

As previously discussed in general terms the present invention is embodied in a method of assembling the head 10, the membrane 11, and encapsulated electrolyte 12. It is also embodied in a fixation ring assembly 52 illustrated in FIG. 5 which permits such assembly to take place without tools and with minimal labor and time consumed.

Referring first to FIG. 2, a sub-assembly 55 of the inner O-ring 13 and a rigid extension ring 57 is illustrated. The rigid extension ring 57 is fabricated of brass having an outside diameter slightly less than the smaller diameter section of the passage 22 through the fixation ring member 20 below the upper shoulder 31. The ring 57 has a downwardly chamfered upper surface 58 and a relatively large diameter passage 59 extending through it.

In the sub-assembly 55 the inner O-ring 13 is stretched outwardly by hand to encircle the rigid brass ring 57. In this relationship, as illustrated in FIG. 2, the O-ring is held in extended relationship for reasons which will hereinafter be discussed.

Turning now to FIG. 3, another sub-assembly 65 comprising the sub-assembly 55 immediately hereinbefore discussed with, in addition, a sponge rubber compression pad 66, is illustrated. In its normal, uncompressed form, the pad 66 is an annular sponge disc formed of closed cell polypropylene or the like. The disc has a diameter slightly larger than the outside diameter of the rigid brass ring 57 in its relaxed, expanded condition. To make the assembly 65 the disc 66 is compressed by hand and inserted into the rigid ring 57 of the assembly 55 to the position illustrated in FIG. 3. The pad will be seen in that position to be compressed into somewhat of an hour glass shape.

The compression pad sub-assembly 65 illustrated in FIG. 3 is then inserted by hand into a fixation ring member 20 as illustrated in FIG. 4. In FIG. 4 it will be seen that the inner O-ring 13 seats in the fixation ring member 20 immediately below the annular lip 30 on the ring member. In this position, it is seated on the shoulder 31. The rigid brass ring 57 is, on the other hand, disposed slightly inwardly of the shoulder 31. The sponge pad 66 is compressed downwardly in the passage 22 against the lower shoulder 32 adjacent the bottom surface 21 of the ring member 20.

Referring now to FIG. 5, a complete, disposable fixation ring assembly 52 is illustrated, as previously pointed out. The assembly 52 is completed by inserting the compression pad sub-assembly 65 into a fixation ring member 20 in the manner just discussed and covering it with a semi-permeable membrane 71.

The membrane 71 is a plastic film fabricated of Mylar, Teflon, or polypropylene or the like. A sheet of the film is drawn tightly over the upper face 23 of the fixation ring member 20. An outer resilient O-ring 75 is then forced downwardly over the sheet and the face 23 to seat with the sheet between the opposed upper and lower shoulders in the annular channel 76 encircling the passage 22 and tightly hold the membrane against the face 23. At the same time the O-ring 75 is sealed, the membrane 71 is serrated around its periphery immediately inside of the O-ring 75, as at 78. In practice, a larger sheet of film is utilized and, after the O-ring 75 is seated to fasten it to the member 20, the film is trimmed.

It will be seen in FIG. 5 that the membrane 71 presses down on the top of the pad 66 when the fixation ring assembly 52 is complete. The assembly 52 is now ready for packaging and distribution as a disposable product.

To use the assembly 52 according to the invention, it is placed on a flat surface as illustrated in FIG. 6. A drop of electrolyte is placed on the sensor head's electrode region. The head 10 is then pressed downwardly onto the membrane 71 and, through it, the pad 66.

As the head 10 is forced downwardly the pad 66 acts through the membrane 71 to force excess electrolyte 12 radially outwardly on the electrode surface. Further downward movement pushes the pad 66 and rigid ring 57 ahead of the electrode surface drawing the membrane more taut and beginning to tear it away from the outer O-ring 75 at the serration line 78. Meanwhile the inner O-ring 13 cannot move downwardly because it is resting on the shoulder 31 and, so, is suddenly released by the rigid ring 57.

When the O-ring 13 is released it immediately contracts. In doing so it completes tearing the film 71 at the serration line 78. The ring 13 contracts to grip the inner annular segment of membrane 11 against the head, encapsulating the electrolyte 12 within the membrane.

Figure 7:
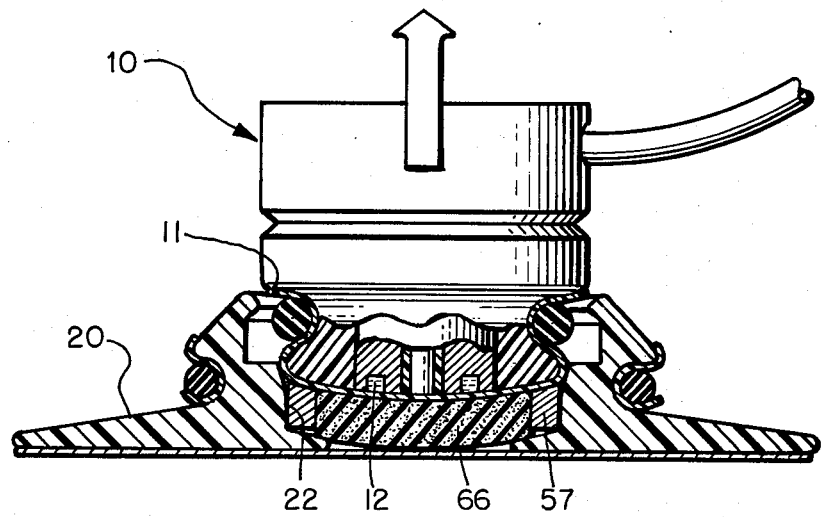
FIG. 7 is a view similar to FIG. 6 with the sensor head-membrane-electrolyte assembly being removed from the fixation ring member passage.

The membrane 11 has now, in effect, been automatically mounted. At this point, referring to FIG. 7, the assembled sensor head 10-membrane 11-electrolyte 12 is lifted out of the fixation ring member 20. The pad 66 and rigid ring 57 assembly remain loose in the passage 22. They are removed and discarded.

The fixation ring member 20 can now be used to attach the head assembly to a patient's skin. Its bottom face is preferably covered with an adhesive protected in a conventional manner by a paper backing. The backing is removed, the patient's skin cleaned, and the ring secured to the skin. The head assembly is then snapped into the ring member 20 and it is ready for use.

While the embodiment described herein is at present considered to be preferred, it is understood that various modifications and improvements may be made therein, and it is intended to cover in the appended claims all such modifications and improvements as fall within the true spirit and scope of the invention.

I claim:

1. A method of assembling a sensor head and permeable membrane encapsulating electrolyte over the electrode surface of the sensor head, for securing to the surface of a patient's skin by means of a fixation ring, wherein the fixation ring has an annular passage extending therethrough from an upper face to a lower face, comprising the steps of:
   a. fastening a sheet of permeable membrane film across the upper face of the fixation ring covering one end of said passage,
   b. placing an electrolyte on at least one of the electrode surface and the membrane film over the passage,
   c. inserting the sensor head into said passage through said one end whereby the membrane is pressed against the base of the sensor head with the electrolyte over the electrode surface, and
   d. causing said membrane to be released from said fixation ring and fastened to said sensor head when said sensor head is inserted.

2. The method of claim 1 further characterized in that:
   a. said membrane is released from said fixation ring by tearing along an annular line defined in the membrane by serrations formed therein.

3. The method of claim 2 further characterized in that:
   a. said membrane is fastened to said sensor head by a resilient ring which contracts against the head with the membrane under it as the membrane tears away from the fixation ring.

4. The method of claim 1 further characterized by:
   a. resiliently pressing the membrane against the base of the sensor head as the sensor head is inserted in said passage.

5. A fixation ring for securing to the surface of a patient's skin, comprising:
   a. a member having a lower face for seating on the skin surface of a patient, and an upper face opposite said lower face,
   b. said member having an annular passage in it opening through both said upper and lower faces,
   c. said passage including a first, largest diameter passage section adjacent said upper face, a second smaller diameter passage section intermediate said faces, and a third, smallest diameter passage section adjacent said lower face,
   d. sensor body detent means formed inwardly of said first passage section adjacent said upper face, and
   e. an annular resilient ring seating channel with opposed shoulders encircling the outside of said member around said passage.

6. A fixation ring assembly for automatically mounting a membrane over the electrode area of a sensor head, comprising:
   a. an annular member having a lower face for seating on the skin surface and an upper face opposite said lower face,
   b. said annular member having an annular passage extending through it opening through both said upper and lower faces,
   c. a compression pad sub-assembly seated in said passage,
   d. said compression pad sub-assembly including a resilient and compressable pad, a substantially rigid annular ring encircling said pad adjacent said upper face, and a resilient compression ring stretched over the annular periphery of said rigid ring so as to be held in extended relationship by said rigid ring, and
   e. a membrane positioned over said passage on said upper face.

7. The fixation ring assembly of claim 6 further characterized in that:
   a. said passage includes a first largest diameter passage section adjacent said upper face, a second smaller diameter passage section intermediate said faces, and a third smallest diameter passage section adjacent said lower face, and
   b. an upper shoulder between said first and second passage sections and a lower shoulder between said second and third passage sections,
   c. said resilient and compressable pad being seated on said lower shoulder.

8. The fixation ring assembly of claim 7 further characterized in that:
   a. said resilient compression ring is normally disposed in said first passage section above said upper shoulder.

9. The fixation ring assembly of claim 8 further characterized by and including:
   a. another resilient compression ring securing said membrane to said annular member over said passage.

10. The fixation ring assembly of claim 9 further characterized in that:
    a. said membrane is serrated along an annular line between said another resilient compression ring and said passage.

* * * * *